US012667099B2

(12) United States Patent
Yanagita et al.

(10) Patent No.: US 12,667,099 B2
(45) Date of Patent: Jun. 30, 2026

(54) CELL PRESERVATION METHOD

(71) Applicant: Cell Exosome Therapeutics Inc.,
Tokyo (JP)

(72) Inventors: Yasutomo Yanagita, Tokyo (JP);
Chugo Rinoie, Tokyo (JP); **Takefumi
Ishidao, Tokyo (JP); Itsunari Minami**,
Tokyo (JP)

(73) Assignee: Cell Exosome Therapeutics Inc.,
Tokyo (JP)

( * ) Notice: Subject to any disclaimer, the term of this
patent is extended or adjusted under 35
U.S.C. 154(b) by 911 days.

(21) Appl. No.: 17/915,415

(22) PCT Filed: Mar. 30, 2021

(86) PCT No.: PCT/JP2021/013685
§ 371 (c)(1),
(2) Date: Sep. 28, 2022

(87) PCT Pub. No.: WO2021/201029
PCT Pub. Date: Oct. 7, 2021

(65) Prior Publication Data
US 2023/0132689 A1     May 4, 2023

(30) Foreign Application Priority Data

Mar. 31, 2020     (JP) ................................. 2020-063821

(51) Int. Cl.
| | |
|---|---|
| *A01N 1/02* | (2006.01) |
| *A01N 1/125* | (2025.01) |
| *A01N 1/142* | (2025.01) |
| *A01N 1/162* | (2025.01) |
| *A61K 9/08* | (2006.01) |
| *A61K 35/28* | (2015.01) |
| *A61K 47/10* | (2017.01) |
| *A61K 47/20* | (2006.01) |
| *C12N 5/0775* | (2010.01) |

(52) U.S. Cl.
CPC ............. *A01N 1/162* (2025.01); *A01N 1/125*
(2025.01); *A01N 1/142* (2025.01); *A61K 9/08*
(2013.01); *A61K 35/28* (2013.01); *A61K 47/10*
(2013.01); *A61K 47/20* (2013.01); *C12N
5/0663* (2013.01); *C12N 2500/35* (2013.01);
*C12N 2500/62* (2013.01)

(58) Field of Classification Search
None
See application file for complete search history.

(56) References Cited

U.S. PATENT DOCUMENTS

| | | | |
|---|---|---|---|
| 5,789,147 A | 8/1998 | Rubinstein et al. | |
| 2004/0058794 A1* | 3/2004 | Dolecek ................ | B04B 5/0428 494/45 |
| 2005/0239196 A1 | 10/2005 | Yanai et al. | |

| | | | |
|---|---|---|---|
| 2006/0212020 A1 | 9/2006 | Rainen et al. | |
| 2008/0199900 A1 | 8/2008 | Signore et al. | |
| 2009/0204071 A1 | 8/2009 | Grant et al. | |
| 2010/0254953 A1 | 10/2010 | Honmou et al. | |
| 2011/0230855 A1 | 9/2011 | Hirabuki | |
| 2011/0274663 A1 | 11/2011 | Shirono et al. | |
| 2011/0274665 A1 | 11/2011 | Maslowski | |
| 2013/0129688 A1 | 5/2013 | Brenner et al. | |
| 2013/0259838 A1 | 10/2013 | Yamanaka et al. | |
| 2013/0295061 A1 | 11/2013 | Maslowski | |
| 2014/0037592 A1 | 2/2014 | Toyoshima et al. | |
| 2014/0193381 A1* | 7/2014 | Warner ............... | A61M 5/1407 422/127 |
| 2015/0118748 A1 | 4/2015 | Ra et al. | |
| 2015/0140656 A1* | 5/2015 | Hernan Izquierdo .. | C12M 45/22 435/307.1 |
| 2017/0006857 A1 | 1/2017 | Yori et al. | |
| 2017/0151288 A1 | 6/2017 | Jeon et al. | |
| 2017/0266234 A1 | 9/2017 | Honmou | |

(Continued)

FOREIGN PATENT DOCUMENTS

| | | |
|---|---|---|
| CN | 109045282 A | 12/2018 |
| JP | H10508314 A | 8/1998 |

(Continued)

OTHER PUBLICATIONS

International Search Report mailed Jun. 22, 2021 for International
Application No. PCT/JP2021/013685, Yanagita et al., "Cell Pres-
ervation Method," filed Mar. 30, 2021 (English translation) (10
pages).
Notification of Reasons for Refusal mailed Jan. 10, 2023 for
Japanese Patent Application No. 2022-512585 (English translation
(machine)) (13 pages).
Office Action mailed Jan. 9, 2024, for Japanese Patent Application
No. 2023-176775, Yanagita et al., "Cell Preservation Method," filed
Oct. 12, 2023 (English machine translation) (9 pages).
Syme et al., "The role of depletion of dimethyl sulfoxide before
autografting: on hematologic recovery, side effects, and toxicity,"
Biol Blood Marrow Transplant. 10(2):135-41 (Feb. 2004).
Office Action dated Nov. 14, 2023, for Japanese Patent Application
No. 2023-078055, Yanagita et al., "Cell Preservation Method," filed
May 10, 2023 (English translation) (13 pages).

(Continued)

*Primary Examiner* — Tracy Vivlemore
*Assistant Examiner* — Fatimah Khalaf Matalkah
(74) *Attorney, Agent, or Firm* — Clark & Elbing LLP

(57) ABSTRACT

The purpose of the present invention is to obtain a cell
suspension with a low concentration of cryoprotectant. This
method of preserving cells used comprises the steps of (a)
enriching cells from a cell suspension containing the cells
and a cryoprotective solution to generate an enriched frac-
tion, and (b) freezing the enriched fraction to prepare a
frozen material. It is also possible to use a method of
producing a cell suspension, comprising the steps of (a)
enriching cells from a cell suspension containing the cells
and a cryoprotective solution to generate an enriched frac-
tion, (b) freezing the enriched fraction to prepare a frozen
material, (c) thawing the frozen material to prepare a thawed
material, and (d) mixing the thawed material and a solution
to produce a cell suspension.

18 Claims, 5 Drawing Sheets

(56)                    References Cited

U.S. PATENT DOCUMENTS

| | | |
|---|---|---|
| 2018/0085406 A1 | 3/2018 | Bernstein et al. |
| 2018/0112013 A1 | 4/2018 | Hayashi et al. |
| 2018/0362922 A1 | 12/2018 | Yamahara et al. |
| 2019/0255118 A1 | 8/2019 | Honmou |
| 2020/0170242 A1 | 6/2020 | Zhang et al. |
| 2021/0301258 A1 | 9/2021 | Imagawa et al. |
| 2022/0267480 A1 | 8/2022 | Hayashi et al. |

FOREIGN PATENT DOCUMENTS

| | | |
|---|---|---|
| JP | 2001-518079 A | 10/2001 |
| JP | 2004-073084 A | 3/2004 |
| JP | 2005-160596 A | 6/2005 |
| JP | 2009-511212 A | 3/2009 |
| JP | 2010-518096 A | 5/2010 |
| JP | 2012-510299 A | 5/2012 |
| JP | 4936341 B2 | 5/2012 |
| JP | 2013-523841 A | 6/2013 |
| JP | 2013-524856 A | 6/2013 |
| JP | 2013-208211 A | 10/2013 |
| JP | 5394932 B2 | 1/2014 |
| JP | 2015-526067 A | 9/2015 |
| JP | 2017-519050 A | 7/2017 |
| WO | WO-98/38940 A1 | 9/1998 |
| WO | WO-2007044980 A2 * | 4/2007 | .......... A61M 5/2425 |
| WO | WO-2008/100498 A2 | 8/2008 |
| WO | WO-2012/108069 A1 | 8/2012 |
| WO | WO-2015/146631 A1 | 10/2015 |
| WO | WO-2016/163444 A1 | 10/2016 |
| WO | WO-2017/073656 A1 | 5/2017 |
| WO | WO-2018/214943 A1 | 11/2018 |
| WO | WO-2020/027163 A1 | 2/2020 |

OTHER PUBLICATIONS

Office Action mailed Aug. 29, 2023, for Japanese Patent Application No. 2023-078055, Yanagita et al., "Cell Preservation Method," filed May 10, 2023 (English translation) (14 pages).

Office Action dated Apr. 2, 2024, for Japanese Patent Application No. 2023-78055, Yanagita et al., "Cell Preservation Method," filed May 10, 2023 (English translation) (11 pages).

* cited by examiner

[Figure 1]

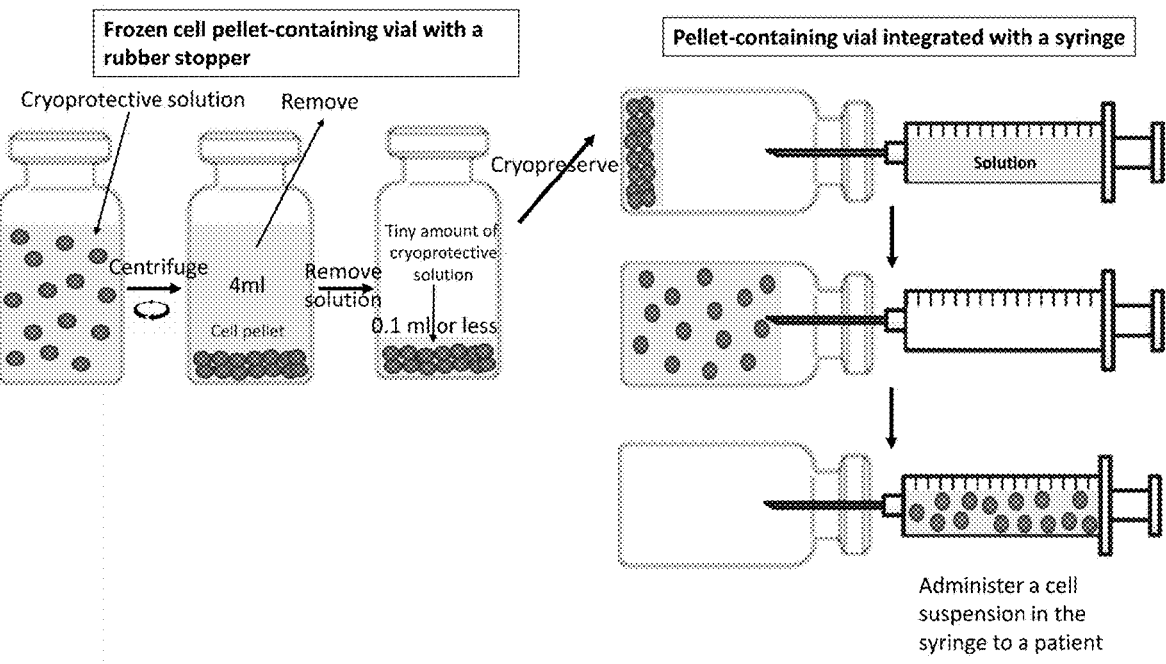

Frozen cell pellet-containing vial with a rubber stopper

Pellet-containing vial integrated with a syringe

Cryoprotective solution    Remove

Centrifuge    4ml    Remove solution    Tiny amount of cryoprotective solution

Cell pellet    0.1 ml or less

Cryopreserve    Solution

Administer a cell suspension in the syringe to a patient

[Figure 2]

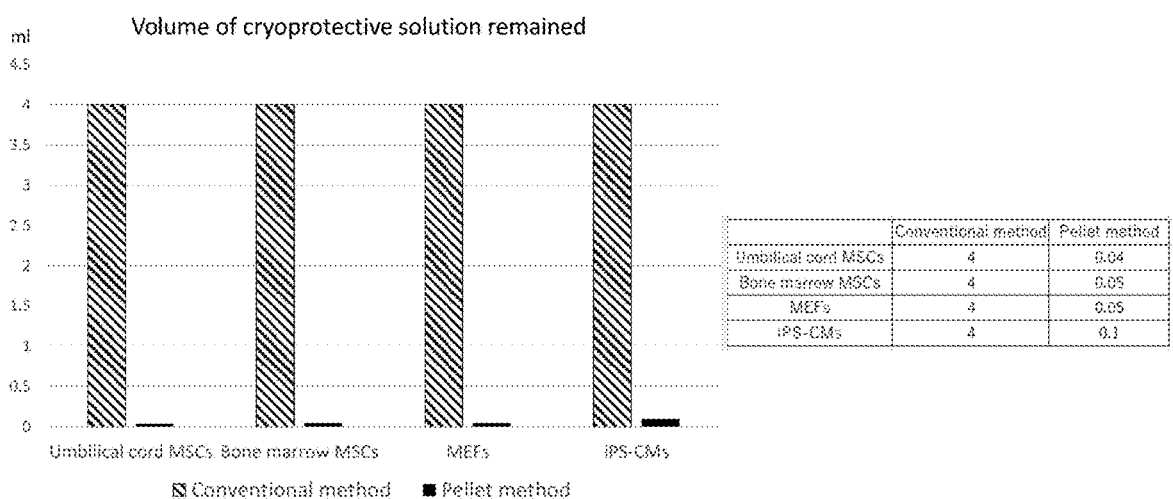

ml    Volume of cryoprotective solution remained

|  | Conventional method | Pellet method |
|---|---|---|
| Umbilical cord MSCs | 4 | 0.04 |
| Bone marrow MSCs | 4 | 0.05 |
| MEFs | 4 | 0.05 |
| iPS-CMs | 4 | 0.1 |

⊠ Conventional method    ■ Pellet method

[Figure 3]
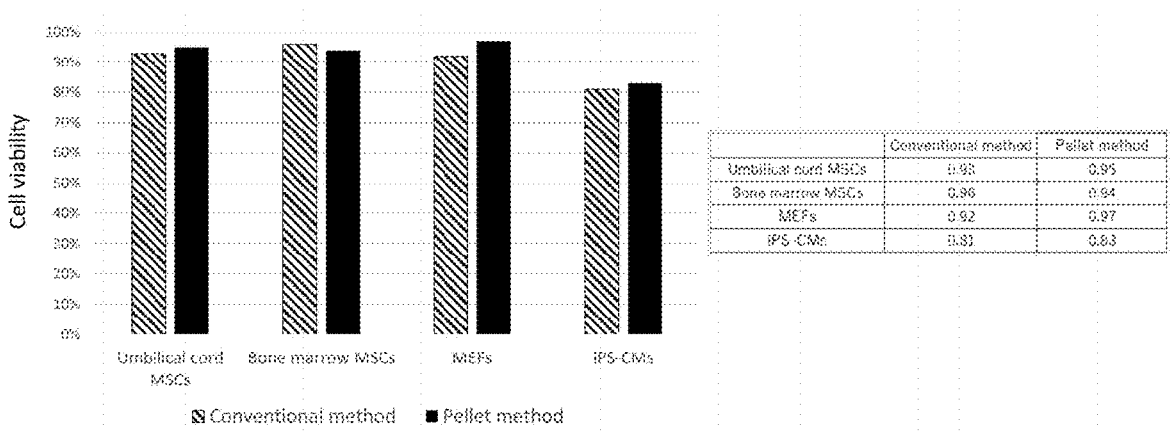
|  | Conventional method | Pellet method |
|---|---|---|
| Umbilical cord MSCs | 0.93 | 0.95 |
| Bone marrow MSCs | 0.96 | 0.94 |
| MEFs | 0.92 | 0.97 |
| iPS-CMs | 0.81 | 0.83 |

[Figure 4]
(A)
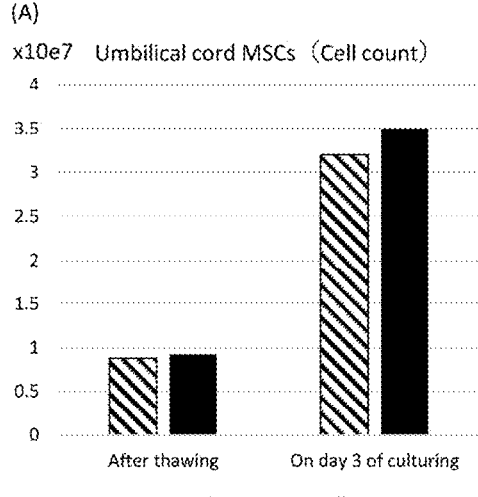
| x10e7 | Conventional method | Pellet method |
|---|---|---|
| After thawing | 0.88 | 0.92 |
| On day 3 of culturing | 3.2 | 3.5 |
(B)
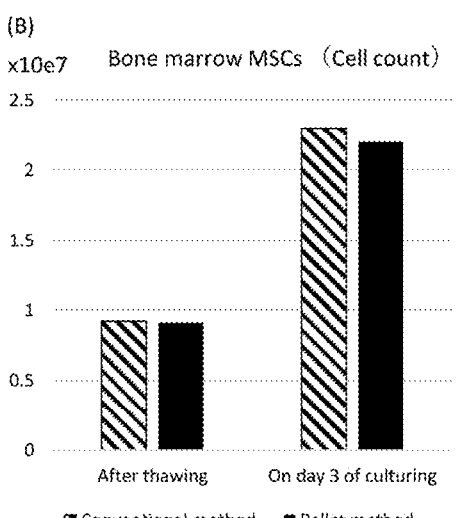
| x10e7 | Conventional method | Pellet method |
|---|---|---|
| After thawing | 0.92 | 0.91 |
| On day 3 of culturing | 2.3 | 2.2 |
(C)
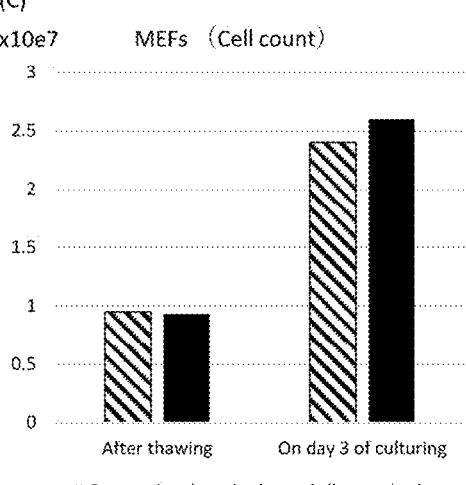
| x10e7 | Conventional method | Pellet method |
|---|---|---|
| After thawing | 0.95 | 0.93 |
| On day 3 of culturing | 2.4 | 2.6 |
(D)
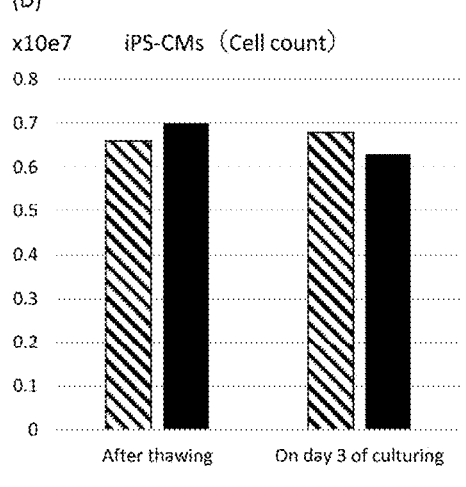
| x10e7 | Conventional method | Pellet method |
|---|---|---|
| After thawing | 0.66 | 0.7 |
| On day 3 of culturing | 0.66 | 0.63 |

[Figure 5]
(a)
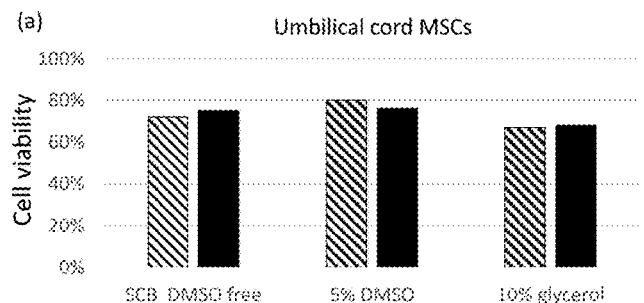
| Cell viability | Conventional method | Pellet method |
|---|---|---|
| SCB_DMSO free | 0.72 | 0.75 |
| 5% DMSO | 0.8 | 0.76 |
| 10% glycerol | 0.67 | 0.68 |
(b)
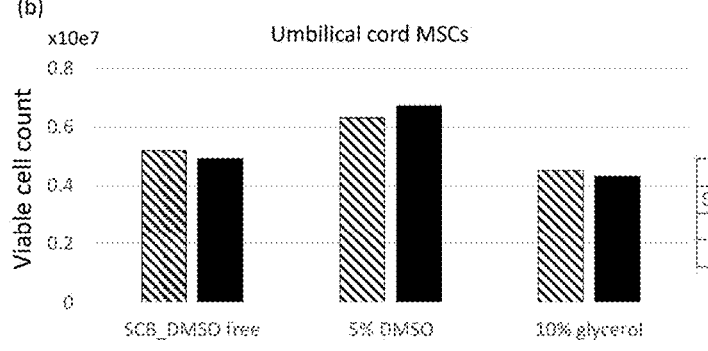
| | Conventional method | Pellet method |
|---|---|---|
| SCB_DMSO free | 0.52 | 0.49 |
| 5% DMSO | 0.63 | 0.67 |
| 10% glycerol | 0.45 | 0.43 |
[Figure 6]
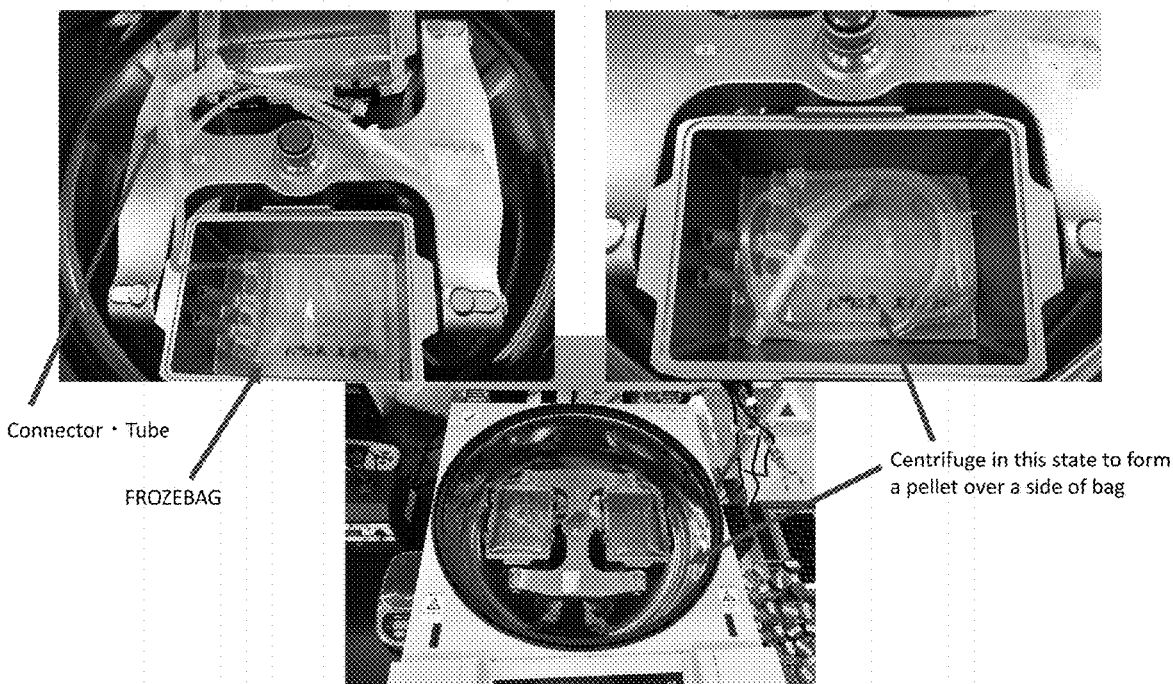
Connector · Tube
FROZEBAG
Centrifuge in this state to form a pellet over a side of bag

[Figure 7]
Volume of cryoprotective solution remained
ml
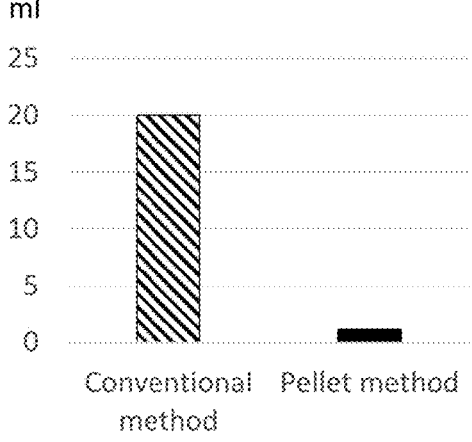
| | Conventional method | Pellet method |
|---|---|---|
| Umbilical cord MSCs | 20 | 1.15 |
[Figure 8]
Umbilical cord MSCs
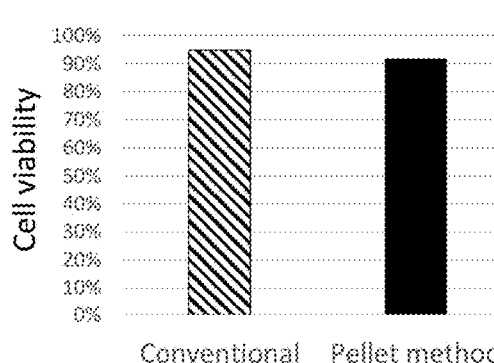
| Cell viability | Conventional method | Pellet method |
|---|---|---|
| Umbilical cord MSCs | 0.95 | 0.92 |
[Figure 9]
Umbilical cord MSCs
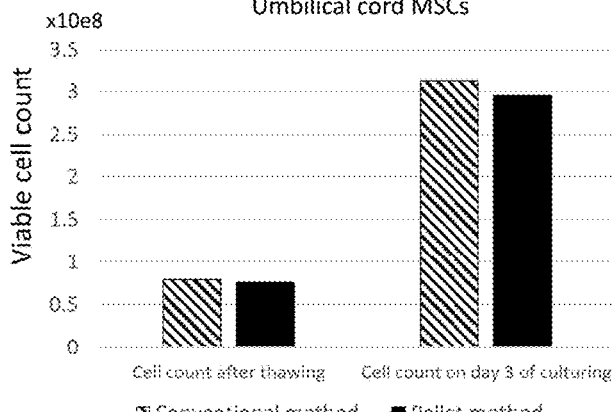
| | Conventional method | Pellet method |
|---|---|---|
| Cell count after thawing | 0.79 | 0.76 |
| Cell count on day 3 of culturing | 3.12 | 2.95 |

CELL PRESERVATION METHOD

TECHNICAL FIELD

The present invention relates to cells, a cell suspension, a container, a device, or a pharmaceutical composition for regenerative medicine.

BACKGROUND ART

Temcell HS Injection and Stemirac Injection are marketed in Japan as stem cell-based products for regenerative medicine. These products are cryopreserved and delivered to medical settings, and are then thawed and administered to patients. The dosage form at the time of administration is a cell suspension.

Temcell HS Injection contains $72 \times 10^6$ human mesenchymal stem cells, 1.08 mL of dimethyl sulfoxide (DMSO), and others in a bag (with a total volume of 10.8 mL). Stemirac Injection contains 0.5 to $2.0 \times 10^8$ autologous bone marrow mesenchymal stem cells, 2 mL or 4 mL of DMSO, and others in a bag (with a total volume of 20 mL or 40 mL). Here, DMSO is a cryoprotectant.

Patent Literature 1 describes a pharmaceutical composition containing human mesenchymal stem cells and a method of producing the same. An application for registration of extension of this patent term concerning Temcell HS Injection has been filed. Patent Literature 2 describes a method of producing a regenerative medicine containing bone marrow- or blood-derived cells. An application for registration of extension of this patent term concerning Stemirac Injection has been filed.

CITATION LIST

Patent Literature

Patent Literature 1: Japanese Patent No. 5394932
Patent Literature 2: Japanese Patent No. 4936341

SUMMARY OF THE INVENTION

Technical Problem

The above regenerative medicine products and the regenerative medicine pharmaceutical compositions described in the Patent Literatures are freeze-thawed and then used. Thus, the cell suspension contains a cryoprotectant. Unfortunately, the fact that the concentration of the cryoprotectant is high may cause adverse side effects.

Solution to Problem

The present inventors have succeeded in producing a cell suspension with a low concentration of cryoprotectant even after freeze-thawing. An aspect of the present invention provides a method of preserving cells, comprising the steps of (a) enriching cells from a cell suspension containing the cells and a cryoprotective solution to generate an enriched fraction, and (b) freezing the enriched fraction to prepare a frozen material. A cell suspension with a low concentration of cryoprotectant may be obtained after a composition containing cells preserved by this method is thawed and suspended in a solution.

Another aspect of the present invention provides a method of freezing and thawing cells, comprising the steps of (a) enriching cells from a cell suspension containing the cells and a cryoprotective solution to generate an enriched fraction, (b) freezing the enriched fraction to prepare a frozen material, and (c) thawing the frozen material to prepare a thawed material.

Still another aspect of the present invention provides a method of producing a frozen cell-containing composition, comprising the steps of (a) enriching cells from a cell suspension containing the cells and a cryoprotective solution to generate an enriched fraction, and (b) freezing the enriched fraction to prepare a frozen material.

Still another aspect of the present invention provides a method of producing a cell suspension, comprising the steps of (a) enriching cells from a cell suspension containing the cells and a cryoprotective solution to generate an enriched fraction, (b) freezing the enriched fraction to prepare a frozen material, (c) thawing the frozen material to prepare a thawed material, and (d) mixing the thawed material and a solution to produce a cell suspension.

Still another aspect of the present invention provides a method of producing a cell suspension, comprising the steps of thawing a frozen material in a container including a cell suspension containing cells and a cryoprotective solution, placing, into the container, a needle attached to a syringe, and injecting a solution from the syringe into the container.

Still another aspect of the present invention provides a container comprising a frozen composition containing a frozen cryoprotectant and a frozen single cell population of $2.0 \times 10^7$ cells/mL or more cells.

Still another aspect of the present invention provides a device comprising a container containing cells and a cryoprotective solution, and a syringe, wherein the container and the syringe are integrated.

Still another aspect of the present invention provides a device comprising a syringe integrated with a container containing a pellet-like cell-containing composition.

Still another aspect of the present invention provides a pharmaceutical composition for regenerative medicine, comprising cells and a cryoprotectant, wherein the cryoprotectant has a content of 1% (v/v) or less.

BRIEF DESCRIPTION OF DRAWINGS

FIG. 1 is a diagram schematically illustrating an example of the pellet method described in Example 1.

FIG. 2 is a graph showing the results of the volume of cryoprotective solution remained in Example 1.

FIG. 3 is a graph showing the results of the cell viability after the cells were frozen and then thawed in Example 1.

FIG. 4 is graphs showing the results of checking the cell count after thawing and the cell count on day 3 of culturing in Example 1.

FIG. 5 is graphs showing the results of checking the cell viability and the cell count after the cells were frozen and then thawed in Example 2.

FIG. 6 is photographs of how a bag was placed in a centrifuge in Example 3.

FIG. 7 is a graph showing the results of examining the volume of cryoprotective solution remained in Example 3.

FIG. 8 is a graph showing the results of the cell viability after the cells were frozen and then thawed in Example 3.

FIG. 9 is a graph showing the results of checking the cell count after thawing and the cell count on day 3 of culturing in Example 3.

DESCRIPTION OF EMBODIMENTS

Hereinafter, embodiments of the invention will be described in detail. Note that repeated descriptions of the same content are omitted, if appropriate, so as to avoid redundancy.

An embodiment of the invention involves a method of preserving cells, comprising the steps of (a) enriching cells from a cell suspension containing the cells and a cryoprotective solution to generate an enriched fraction, and (b) freezing the enriched fraction to prepare a frozen material. A cell suspension with a low concentration of cryoprotectant may be obtained after a composition containing cells preserved by this method is thawed and suspended in a solution. Cells under preservation by this method can be stored in a container (e.g., in a freezer) until use for their intended purpose (e.g., administration of the cells to a patient(s) in regenerative medicine). For example, when used in regenerative medicine, cells preserved by this method can be taken out from a freezer before administered to a patient, thawed, suspended in a solution, and administered to the patient. In this case, depending on the volume of suspension, the cryoprotectant in the suspension can be set to a low concentration. This makes it possible to administer a cell suspension with superior safety. Also, since the cells are concentrated in advance, the cells at a desired concentration can remain in the suspension.

An embodiment of the invention involves a method of preserving cells, comprising the steps of: centrifuging a container containing cells and a cryoprotective solution to separate a supernatant from a precipitate; removing the supernatant to generate an enriched fraction; and freezing the enriched fraction. A cell suspension with a low concentration of cryoprotectant may be obtained after a composition containing cells preserved by this method is thawed and suspended in a solution.

An embodiment of the invention includes a method of freezing and thawing cells, comprising the steps of (a) enriching cells from a cell suspension containing the cells and a cryoprotective solution to generate an enriched fraction, (b) freezing the enriched fraction to prepare a frozen material, and (c) thawing the frozen material to prepare a thawed material. A cell suspension with a low concentration of cryoprotectant may be obtained after cells preserved and thawed by this method are suspended in a solution.

An embodiment of the invention includes a method of freezing and thawing cells, comprising the steps of suspending single cells in a cell cryoprotective solution, centrifuging the cells to form a pellet, and freezing and thawing the remaining cell pellet after a supernatant has been removed from the cryoprotective solution. A cell suspension with a low concentration of cryoprotectant may be obtained after cells preserved and thawed by this method are suspended in a solution.

An embodiment of the invention involves a method of producing a frozen cell-containing composition, comprising the steps of (a) enriching cells from a cell suspension containing the cells and a cryoprotective solution to generate an enriched fraction, and (b) freezing the enriched fraction to prepare a frozen material. A cell suspension with a low concentration of cryoprotectant may be obtained after a frozen cell-containing composition obtained by this production method is thawed and suspended in a solution. In this case, depending on the volume of suspension, the cryoprotectant in the suspension can be set to a low concentration. This makes it possible to obtain a cell suspension with superior safety. Also, since the cells are concentrated in advance, the cells at a desired concentration can remain in the suspension.

An embodiment of the invention involves a method of producing a frozen cell-containing composition, comprising the steps of: centrifuging a container containing cells and a cryoprotective solution to separate a supernatant from a precipitate; removing the supernatant to generate an enriched fraction; and freezing the enriched fraction. A cell suspension with a low concentration of cryoprotectant may be obtained after a frozen cell-containing composition obtained by this production method is thawed and suspended in a solution.

An embodiment of the invention includes a method of producing a cell suspension, comprising the steps of (a) enriching cells from a cell suspension containing the cells and a cryoprotective solution to generate an enriched fraction, (b) freezing the enriched fraction to prepare a frozen material, (c) thawing the frozen material to prepare a thawed material, and (d) mixing the thawed material and a solution to produce a cell suspension. This production method allows for a cell suspension with a low concentration of cryoprotectant.

An embodiment of the invention involves a method of producing a cell suspension, comprising the steps of: centrifuging a container containing cells and a cryoprotective solution to separate a supernatant from a precipitate; removing the supernatant to generate an enriched fraction; freezing the enriched fraction; and mixing the resulting frozen material and a solution to produce a cell suspension. This production method allows for a cell suspension with a low concentration of cryoprotectant.

An embodiment of the invention involves a method of producing a cell suspension, comprising the steps of freezing an enriched fraction obtained by enriching cells to produce a frozen material or thawing a frozen enriched fraction obtained by enriching cells to produce a thawed material. This production method allows for a cell suspension with a low concentration of cryoprotectant.

An embodiment of the invention includes a method of producing a cell suspension, comprising the steps of thawing a frozen material in a container including a cell suspension containing cells and a cryoprotective solution, placing, into the container, a needle attached to a syringe, and injecting a solution from the syringe into the container. This production method allows for a cell suspension with a low concentration of cryoprotectant.

An embodiment of the invention involves a method of producing a container including a frozen cell-containing composition, comprising the steps of (a) enriching cells from a cell suspension containing the cells and a cryoprotective solution to generate an enriched fraction, and (b) freezing the enriched fraction to prepare a frozen material. A cell suspension with a low concentration of cryoprotectant may be obtained after a frozen cell-containing composition in a container as obtained by this production method is thawed and suspended in a solution.

An embodiment of the invention involves a method of producing a frozen cell-containing composition, comprising the steps of (a) enriching cells from a cell suspension containing the cells and a cryoprotective solution to generate an enriched fraction. A cell suspension with a low concentration of cryoprotectant may be obtained after a frozen cell-containing composition obtained by this production method is thawed and suspended in a solution.

An embodiment of the invention involves a method of producing a cell pellet, comprising the steps of: centrifuging the above-described container containing cells and a cryoprotective solution to separate a supernatant from a precipitate; and removing the supernatant to generate an enriched fraction. The cell pellet obtained by this production method may be frozen and thawed to produce a cell pellet.

An embodiment of the invention includes a device comprising: a rubber stopper-attached vial containing the above-described cell pellet; and a syringe having a cell suspension, wherein the syringe and the vial are combined and shaped such that a needle attached to the syringe is pierced into the rubber stopper.

An embodiment of the invention includes a method of producing a cell-containing composition or a method comprising the step of (a) enriching cells from a cell suspension containing the cells and a cryoprotective solution to generate an enriched fraction, or (b) freezing the enriched fraction to prepare a frozen material.

An embodiment of the invention includes a container comprising a frozen composition containing a frozen cryoprotectant and a frozen single cell population of $2.0 \times 10^7$ cells/mL or more cells (e.g., stem cells). The frozen material contained in this container may be thawed and then mixed with a solution. In this case, a cell suspension can be prepared while the cryoprotectant is diluted according to the volume of solution. This container may be produced by the production method of one of the above embodiments of the invention. Here, the cell concentration in the composition may be $2.0 \times 10^7$, $3 \times 10^7$, $4 \times 10^7$, $5 \times 10^7$, $6 \times 10^7$, $7 \times 10^7$, $1 \times 10^8$, $3 \times 10^8$, $5 \times 10^8$, $7 \times 10^8$, $9 \times 10^8$, or $1 \times 10^9$/mL or higher, or may be a number between any two of them. The above composition may contain a cryoprotectant in a concentration of 20% (v/v) or less. This concentration may be, for example, 0.5, 1, 2, 3, 4, 5, 6, 7, 8, 9, 10, 15, or 20% (v/v), or may be a number between any two of them. The cryoprotectant may be, for example, DMSO, glycerol, glycerin, dextran, polyethylene glycol, ethylene glycol, propylene glycol, or propanediol. If the cryoprotectant is trehalose, sorbitol, or polyvinylpyrrolidone, the concentration, namely the content of the cryoprotectant may be 20% (w/v) or less. This concentration may be, for example, 0.5, 1, 2, 3, 4, 5, 6, 7, 8, 9, 10, 15, or 20% (w/v), or may be a number between any two of them. The above composition may contain 0.001 to 1 mL of cryoprotectant. This volume may be, for example, 0.001, 0.005, 0.01, 0.05, 0.1, 0.2, 0.3, 0.4, 0.5, 0.6, 0.7, 0.8, 0.9, or 1 mL, or may be a number between any two of them.

An embodiment of the invention includes a container containing a frozen composition containing frozen cells and a frozen cryoprotective solution, wherein the volume of the frozen composition is 30% or less of the volume of the container. The frozen composition contained in this container may be thawed and then mixed with a solution. In this case, a cell suspension may be prepared while the cryoprotectant is diluted according to the volume of solution. At that time, the solution can be injected into part that is in the container but is other than the frozen composition. Therefore, the cell suspension can be simply prepared.

An embodiment of the invention includes a device comprising a container of one of the above embodiments of the invention and a syringe, wherein the container and the syringe are integrated. This device can be used to simply prepare a cell suspension. In addition, this device may be used to produce a cell suspension with a low concentration of cryoprotectant. In one embodiment of the invention, the integration includes a connected state. In one embodiment of the invention, the connection includes a form of direct or indirect connection. In the case of direct connection, for example, a surface of the container and the syringe may be directly connected. In the case of indirect connection, for example, the container and the syringe may be connected via a coupling part (e.g., a tube, a connector). At this time, a surface of the container is connected to the coupling part, and the coupling part may then be connected to the syringe.

An embodiment of the invention includes a composition containing a cryoprotectant and $2.0 \times 10^7$ cells/mL or more cells (e.g., stem cells). Here, the cells should be a population of single cells. At this time, the concentration of cryoprotectant is not limited as long as the concentration is effective in cryoprotecting cells. This concentration may be, for example, 0.5 to 20% (v/v) or 0.5 to 20% (w/v). When this composition is frozen and the resulting frozen composition is thawed and then mixed with a solution, a cell suspension can be prepared while the cryoprotectant is diluted in accordance with the volume of the solution. The concentrations of cells and cryoprotectant in this composition may each be in the range of values listed in the description of the composition in the container above. This composition can be produced by the production method of one of the above embodiments of the invention. An embodiment of the invention includes a container containing the above composition.

An embodiment of the invention includes a device comprising a container containing the above composition and a syringe, wherein the container and the syringe are integrated. This device can be used to simply prepare a cell suspension. In addition, this device may be used to produce a cell suspension with a low concentration of cryoprotectant.

An embodiment of the invention includes a device comprising a syringe and a container including a pellet-like cell (e.g., stem cell)-containing composition, wherein the container and the syringe are integrated. This device can be used to simply prepare a cell suspension. An embodiment of the invention includes a device comprising a syringe and a container including a frozen composition containing frozen cells (e.g., stem cells), wherein the container and the syringe are integrated. In addition, this device may be used to produce a cell suspension with a low concentration of cryoprotectant.

An embodiment of the invention includes a frozen composition, container, or device of one of the above embodiments of the invention. This frozen material may be used to produce a cell suspension with a low concentration of cryoprotectant. The frozen container including a frozen cell-containing composition or a frozen device in which the container and a syringe are integrated can be distributed while kept in a frozen state. The frozen device in which the container and a syringe are integrated has an advantage of capable of omitting the step of connecting the container and the syringe at a medical site.

An embodiment of the invention includes a composition (e.g., a pharmaceutical composition for regenerative medicine) containing cells (e.g., human stem cells) and a low concentration of cryoprotectant. The concentration of cryoprotectant in this composition may be, for example, 1% (v/v) or less or 1% (w/v) or less. This composition has a low concentration of cryoprotectant and is thus safe when administered to a subject. This concentration of cryoprotectant may be, for example, the concentration at the time of administration to a patient. In one embodiment of the invention, 1% (v/v) or less or 1% (w/v) or less may be, for example, $1 \times 10^{-6}$, $1 \times 10^{-5}$, $1 \times 10^4$, $1 \times 10^{-3}$, $1 \times 10^{-2}$, $1 \times 10^{-1}$, 0.2, 0.3, 0.4, 0.5, or 1% (v/v) or % (w/v), or may be a number between any two of them. An embodiment of the invention involves use of cells for the manufacture of a composition for regenerative medicine, wherein the composition for regenerative medicine contains a low concentration of cryoprotectant. An embodiment of the invention includes a composition containing cells for use in regenerative medicine, wherein the composition contains a low concentration of cryoprotectant. In one embodiment of the invention, in regenerative medicine, a composition containing cells and a cryoprotectant (e.g., at a concentration of 1% (v/v) or less) may be administered to a subject. The regenerative medicine also includes cell therapy. The cell therapy includes a treatment method comprising the step of administering cells to a subject.

An embodiment of the invention includes a method of regenerative medicine, comprising the step of administering to a patient a regenerative medicine-use composition containing cells (e.g., human stem cells), wherein a cryoprotectant in the regenerative medicine-use composition is at a low concentration. The concentration of the cryoprotectant at that time may be, for example, 1% (v/v) or less or 1% (w/v) or less. This method of regenerative medicine has excellent safety because the concentration of cryoprotectant administered is low. The administration may be, for example, intravascular (e.g., intravenous or intra-arterial) administration. The administration may be conducted by infusion.

An embodiment of the invention includes a method of regenerative medicine, comprising the steps of: enriching cells from a cell suspension containing the cells and a cryoprotective solution to generate an enriched fraction; freezing the enriched fraction to prepare a frozen material; thawing the frozen material to prepare a thawed material; mixing the thawed material and a solution to produce a cell suspension; and administering the cell suspension to a subject.

An embodiment of the invention includes a method of regenerative medicine, comprising the steps of: thawing a frozen composition according to any one of the above embodiments of the invention in a container; adding a solution to the above container to suspend cells; or administering the above cell suspension to a subject.

According to an embodiment of the invention, a method of preserving cells, a method of freezing and thawing cells, a method of producing a frozen cell-containing composition, a method of producing a cell suspension, a method of producing a container, or a method of producing a cell pellet may comprise the steps of: culturing the cells; dispersing the resulting cell colony into single cells (e.g., with a trypsin-containing solution); centrifuging the resulting population of single cells to generate a precipitate fraction; or mixing the precipitate fraction with a cryoprotective solution.

According to an embodiment of the invention, a method of preserving cells, a method of freezing and thawing cells, a method of producing a frozen cell-containing composition, a method of producing a cell suspension, a method of producing a container, or a method of producing a cell pellet may comprise the step of mixing cells and a cryoprotective solution to produce a cell suspension. After this step, the cell suspension may be allowed to stand. The incubation time may be 1, 2, 3, 4, 5, 10, 20, 30, or 60 min or longer, or may be a number between any two of them. From the viewpoint of obtaining higher cell viability after freezing and thawing, the incubation time should be at least 5 min. The temperature at that time may be, for example, 3, 4, 5, 6, 10, 20, 30, or 37° C., or may be a number between any two of them.

According to an embodiment of the invention, the method or production method (e.g., the method of preserving cells, the method of freezing and thawing cells, the method of producing a frozen cell-containing composition, the method of producing a cell suspension, the method of producing a container, or the method of producing a cell pellet) may comprise the steps of: centrifuging a container containing cells and a cryoprotective solution to separate a supernatant from a precipitate; and removing the supernatant to prepare an enriched fraction. This two steps may be used to generate a cell-enriched fraction by a simple procedure. In addition, highly concentrated cells and an effective amount of cryoprotectant for cryoprotection may be included in the enriched fraction.

According to an embodiment of the invention, the method or production method (e.g., the method of preserving cells, the method of freezing and thawing cells, the method of producing a frozen cell-containing composition, the method of producing a cell suspension, the method of producing a container, or the method of producing a cell pellet) may comprise the step of using a filter to enrich cells from a cell suspension containing the cells and a cryoprotective solution. This step makes it possible to include highly concentrated cells and an effective amount of cryoprotectant for cryoprotection in the enriched fraction.

According to an embodiment of the invention, the method or production method (e.g., the method of preserving cells, the method of freezing and thawing cells, the method of producing a frozen cell-containing composition, the method of producing a cell suspension, the method of producing a container, or the method of producing a cell pellet) may comprise the step of placing a container containing the enriched fraction under a freezing point environment. The method or production method may comprise the step of connecting a syringe with a container containing the above-mentioned enriched fraction (e.g., by placing a syringe-attached needle into the container) to form a device where the above container and syringe are integrated. The method or production method may comprise the step of freezing the above device. The method or production method may comprise the step of placing the above device under a freezing point environment. The method or production method may comprise the step of storing the above frozen material in a freezer. The method or production method may comprise the step of injecting a solution from the above syringe into the above container. The method or production method may comprise the step of repeatedly conducting charge into and discharge from a syringe. The method or production method may comprise the step of aspirating, with a syringe, the above cell suspension in a container. The method or production method may comprise the step of separating the syringe from the container. The method or production method does not have to comprise, between steps (a) and (b), the step of culturing or washing the cells, adding a cryoprotectant to the container, or adding culture medium, buffer solution, or saline to the container.

The terms described in the above embodiments are each explained in more detail below.

In one embodiment of the invention, the syringe may contain a pharmaceutically acceptable carrier or a frozen material thereof. The syringe may contain, for example, saline, buffer solution (e.g., PBS), or a frozen equivalent.

In one embodiment of the invention, the enriched fraction may contain cells and a cryoprotective solution. The enriched fraction may be contained in a vial or bag.

In one embodiment of the invention, the enrichment may be five-fold or higher. This fold may be, for example, 5, 10, 20, 30, 40, 50, 60, 70, 100, 120, 150, 200, 300, or 400 times or more, or may be a number between any two of them.

In one embodiment of the invention, the cells may exist as a cell population. The cells may also be a population of single cells. The population of single cells includes cells that are not attached to each other and are in a single state. The single-cell population may be generated, for example, by treating the cell population with a cell-dispersing agent (e.g., trypsin). Examples of the single-cell population include a cell population predominantly composed of single cells. Examples of the single-cell population-containing composition include a form of cell dispersion. The single-cell population may be observed, for example, under a microscope. The single-cell population may also be analyzed with a cell sorter. The single-cell population has higher cell viability after thawing in the method or production method according to one of the above embodiments of the invention. The cell viability after thawing may be, for example, 75, 80, 85, 90, 95, 96, 97, 98, 99, or 100%, or may be a number between any two of them.

In one embodiment of the invention, the cells may be, for example, mammalian cells. Examples of the mammal include animals such as humans, monkeys, or rodents (e.g., mice, hamsters). The cells include stem cells or somatic cells. Examples of the stem cells include cells with self-renewal potential and potential to differentiate into different cell types. Examples of the stem cells include pluripotent stem cells, multipotent stem cells, or unipotent stem cells. Examples of the pluripotent stem cells include ES cells or iPS cells. Examples of the multipotent stem cells include mesenchymal stem cells, adipose stem cells, hematopoietic stem cells, or neural stem cells. Examples of the unipotent stem cells include muscle stem cells or pigment stem cells. Examples of the somatic cells include cells derived from the heart, skin, liver, lung, stomach, intestine, kidney, uterus, brain, blood, or mesenchymal tissue. Other examples of the somatic cells include fibroblasts or blood cells (e.g., leukocytes (e.g., T cells, dendritic cells, NK cells), erythrocytes, platelets). These cells may be genetically modified cells (e.g., CAR-T cells). These cells can be applied to the method including steps (a) and (b) above, resulting in a cell suspension with excellent safety and favorable cryopreservation efficiency.

In one embodiment of the invention, examples of the cryoprotectant include DMSO, glycerol, dextran, polyethylene glycol, ethylene glycol, propylene glycol, glycerin, polyvinylpyrrolidone, propanediol, trehalose, or sorbitol. The cryoprotectant may be produced by known procedures. The cryoprotectant may be commercially available and may be purchased from manufacturers (e.g., Zenoaq Resource Co., Ltd., FUJIFILM Wako Pure Chemical Corporation, TOKYO CHEMICAL INDUSTRY CO., LTD.). Examples of the trehalose include $\alpha,\alpha$-trehalose, $\alpha,\beta$-trehalose, $\beta,\beta$-trehalose, glucosyl trehalose, maltosyl trehalose, or maltotriosyl trehalose. Examples of the dextran include dextran 40 or dextran 70.

In one embodiment of the invention, the regenerative medicine includes medical practice of treating a disease by administering cells to a patient with the disease. Examples of the regenerative medicine include treatment of administering human mesenchymal stem cells to each patient with acute graft-versus-host disease (e.g., after hematopoietic stem cell transplantation). Examples of the regenerative medicine also include treatment of administering (e.g., autologous) bone-marrow mesenchymal stem cells to each patient with neurological syndrome or dysfunction associated with spinal cord injury. The route of administration to the patient may be, for example, intravenous.

In one embodiment of the invention, the composition (e.g., a cell suspension, a pharmaceutical composition for regenerative medicine) may contain a pharmaceutically acceptable carrier. The composition may contain cells (e.g., stem cells) at $1.0\times10^5$ cells/mL or more. This concentration may be, for example, $1.0\times10^5$, $1.0\times10^6$, $1.0\times10^7$, $1.0\times10^8$, or $1.0\times10^9$ cells/mL or higher, or may be a number between any two of them. The composition may contain a cryoprotectant at $1\times10^{-6}$ to 0.5% (v/v) or $1\times10^{-6}$ to 0.5% (w/v). This concentration may be, for example, $1\times10^{-6}$, $1\times10^{-5}$, $1\times10^4$, $1\times10^{-3}$, $1\times10^{-2}$, $1\times10^{-1}$, 0.2, 0.3, 0.4, or 0.5% (v/v) or % (w/v), or may be a number between any two of them. This composition may be contained in a syringe or bag. The concentration of cells or cryoprotectant in this composition may be, for example, the concentration at the time of administering the composition to a patient.

In one embodiment of the invention, the freezing may be slow freezing or quick freezing. Examples of the slow freezing include a procedure for freezing cells by cooling them at a slow cooling rate over a long period of time. For the slow freezing, for example, a BICELL (Japan Freezer Co., Ltd.) may be used; freezing control by a programmed freezer may be used; or a heat insulator Styrofoam box may be used. The slow freezing may be performed, for example, at a rate of 0.1 to 1° C./min. The "0.1 to 1° C./min" may be, for example, 0.1, 0.2, 0.3, 0.4, 0.5, 0.6, 0.7, 0.8, 0.9, or 1° C./min, or may be a number between any two of them. Examples of the quick freezing include a procedure for quick freezing in liquid nitrogen and preservation. The freezing is preferably slow freezing. This case excels in terms of maintaining the number of viable cells after freezing and thawing. The freezing may be caused by placing or storing the above container, suspension, or composition below freezing point. The temperature below freezing point may be, for example, −50, −60, −80, −100, −120, or −140° C. or less, or may be a number between any two of them. The freezing time may be, for example, 3, 6, 12, 18, 24, 30, 36, 42, 48, 72, or 96 h or longer, or may be a number between any two of them.

In one embodiment of the invention, the step of removing the supernatant after centrifugation from the container may comprise the step of aspirating the supernatant in the container with a pipette, or aspirating the supernatant in the container with a syringe connected to the container. When the post-centrifugation supernatant is removed from the container, part of the supernatant may be removed. The part may be 80, 90, 95, 96, 97, 98, 99, 99.5% or more, may be a number between any two of them, and may be less than 100%.

In one embodiment of the invention, the centrifugal force of the centrifugation performed on a container containing a mixture of cells and a cryoprotective solution may be, for example, 150, 200, 250, 300, 350, 400, 450, 500, 600, or 700 g, or may be a number between any two of them. The centrifugation time may be, for example, 2, 3, 4, 5, 6, 7, 8, 9, 10, or 15 min or less, or may be a number between any two of them. A plate centrifuge may be used to centrifuge the bag.

In one embodiment of the invention, examples of the container include a vial, a bag, or a bottle. Examples of the container include a container having a stopper through which a needle attached to a syringe can penetrate. Examples of the stopper include a rubber stopper. The rubber stopper is likely to keep a closed system when the needle is placed. Examples of a material for the container include glass or plastic. Examples of the plastic include polypropylene, polyethylene, or an ethylene-vinyl acetate copolymer. When a solution is charged from the syringe into the container, the solution may be charged while releasing air (e.g., from the end of the rubber stopper). Examples of the vial include a bottle-type vessel that can hold a solution (e.g., a cell suspension). Examples of the vial include a sterile vial (e.g., a vial with a sterile solution compartment) or a vial for cryopreservation. The bag has a superior shape to keep a closed system. When the bag is used, the shape of the bag can be changed in response to the volume of liquid or gas in the container. Thus, the solution can be easily injected from the syringe into the container. When the bag is used, the amount of gas in the bag may be reduced before the cell-containing composition in the bag is frozen. Examples of the bag include a sterile bag (e.g., a bag with a sterile solution compartment), a cryopreservation bag, an infusion bag, a soft bag, or a bag with tubing attached. The bag may be connected directly or indirectly to the syringe. In the case of direct connection, for example, an opening of the bag and the syringe may be directly connected. In the case of indirect connection, for example, the bag and the syringe may be connected via a coupling part (e.g., a tube, a connector). At this time, an opening of the container is connected to the coupling part, and the coupling part may then be connected to the syringe. The volume of the solution with which the container can be filled may be, for example, 1, 2, 3, 4, 5, 10, 15, 20, 25, 30, 50, 100, 500, 1000, or 1500 mL or more, or may be a number between any two of them.

In one embodiment of the invention, a device where the container and syringe are integrated may be configured such that a needle attached to the syringe passes through a surface of the container. The container surface part through which the needle passes may be made of rubber.

In one embodiment of the invention, the size of injection needle may be, for instance, 18G or larger. This size may be, for example, 18, 19, 20, 21, 22, 23, 24, 25, 26, or 27G, or may be a number between any two of them. Preferred is from 21 to 23G from the viewpoint of how easily the cells can be suspended when a solution is injected from the syringe into the container and how low the cells receive stress. In one embodiment of the invention, the volume of solution with which the syringe can be filled may be, for example, 1, 5, 10, 15, 20, 50, 100, 200, 300, 400, or 500 mL or more, or may be a number between any two of them. The syringe may be equipped with a plunger.

In one embodiment of the invention, the cell thawing time may be, for example, 1, 2, 3, 4, or 5 min or longer, or may be a number between any two of them. The thawing may include melting.

All the literatures and (patent or patent application) publications cited herein are incorporated by reference in their entirety.

As used herein, the term "or" is used when "at least one" matter listed in the text is acceptable. The same applies to "or". When the wording "number between any two" is indicated herein, this range encompasses the two numbers inclusive. The wording "from A to B" herein means A or more and B or less.

Hereinabove, embodiments of the invention have been described. However, they are examples of the invention. Hence, various configurations other than the above can be adopted. In addition, the configurations described in the above embodiments may be combined and adopted.

EXAMPLES

Hereinbelow, the invention will be described in more detail with reference to Examples.

However, the invention is not limited to them.

Example 1

Four cell types (umbilical cord-derived mesenchymal stem cells (umbilical cord MSCs, provided by CET), bone marrow-derived mesenchymal stem cells (bone marrow MSCs, Lonza, PT-3001), mouse embryonic fibroblasts (MEFs, Chemicon International), or iPS cell-derived cardiomyocytes (iPS-CMs, Myoridge, H-013506)) were subjected to a conventional freezing and thawing method (hereinafter, referred to as the conventional method) or a freezing and thawing method using enriched cells (hereinafter, referred to as the pellet method). Here, the cell viability after thawing and the cell count after thawing were compared with the cell count on day 3 of culturing.

1.1 Experimental Procedure 1.1.1 Conventional Method

Each conical tube containing various types of cells (1×10e7 cells) made into single cells by trypsin solution or TrypLE™ Select solution (Thermo Fisher) was centrifuged at 400 g×5 min. The trypsin solution in the supernatant was removed by decantation using a tip, and replaced with 4 ml of ZENOAQ's Stem Cell Banker (used for umbilical cord MSCs or bone marrow MSCs) cryoprotectant (10% (v/v) DMSO), or Cell Banker 1 plus (used for MEFs or iPS-CMs) cryoprotectant (10% (v/v) DMSO). The total volume of the resulting cell suspension was transferred to a vial with a rubber stopper (5-111-02, manufactured by Maruemu Corporation; volume: 5 ml), and then subjected to slow freezing overnight in a BICELL (Japan Freezer), which is a container for slow freezing, in a freezer at −80° C. The vial was then warmed for thawing at 37° C. for several minutes. Subsequently, 16 ml of PBS was added for dilution to the vial for recovery. The cell suspension was transferred to a centrifuge tube, and the cell viability and the cell count were measured with a cell counter. Next, the cell suspension was centrifuged at 400 g×5 min to continue cell culture evaluation. The PBS in the supernatant was then removed. After an appropriate amount of each cell culture medium was added, the cells were suspended by pipetting, seeded on a culture dish, and cultured for 3 days. The cells were made into single cells by using a trypsin solution, and the number of cells was recounted.

1.1.2 Pellet Method

FIG. 1 is a schematic diagram illustrating an example of the pellet method. Each conical tube containing various types of cells (1×10e7 cells) made into single cells by trypsin solution or TrypLE™ Select solution was centrifuged at 400 g×5 min. The trypsin solution in the supernatant was removed by decantation using a tip, and replaced with 4 ml of ZENOAQ's Stem Cell Banker (used for umbilical cord MSCs or bone marrow MSCs) cryoprotectant (10% (v/v) DMSO), or Cell Banker 1 plus (used for MEFs or iPS-CMs) cryoprotectant (10% (v/v) DMSO). The total volume of the resulting cell suspension was transferred to a vial with a rubber stopper (5-111-02, manufactured by Maruemu Corporation; volume: 5 ml), allowed to stand in a refrigerator at 4° C. for 5 min, and then centrifuged at 400 g×5 min to form a cell pellet. After that, a 1000 μl tip and a 20-μl tip were used to remove as much the cryoprotective solution in the supernatant as possible (3.9 to 3.96 ml in total was removed), followed by overnight slow freezing in a −80° C. freezer in a BICELL, which is a container for slow freezing. The vial was then warmed for thawing at 37° C. for several minutes. A syringe filled with 16 ml of PBS and a 21G needle were used; the needle was placed through the rubber stopper; and PBS was then added. The vial was lightly tapped, so that the pellet was made to float. The cell suspension was then slowly aspirated with the needle to collect the cells. The cell suspension was transferred to a centrifuge tube, and the cell viability and the cell count were measured with a cell counter. Next, the cell suspension was centrifuged at 400 g×5 min to continue cell culture evaluation. The PBS in the supernatant was then removed. After an appropriate amount of each cell culture medium was added, the cells were suspended by pipetting, seeded on a culture dish, and cultured for 3 days. The cells were made into single cells by using a trypsin solution, and the number of cells was recounted.

1.2 Results of Experiments 1.2.1 Volume of Cryoprotective Solution Remained

In the conventional method or the pellet method, the volume of cryoprotective solution remained at the time of cell freezing was calculated from the volume of cryoprotective solution removed from the vial, and plotted in a graph (FIG. 2). In the pellet method, the volume of cryoprotective solution remained was reduced to $\frac{1}{40}$ to $\frac{1}{100}$ of that in the conventional method.

1.2.2 Cell Viability and Cell Count

In the conventional method and the pellet method, the cell viability after cell thawing was measured with a cell counter (FIG. 3). The results showed no significant difference between the two groups.

In the conventional method and the pellet method, the cell count after thawing and the cell count on day 3 of culturing were measured with a cell counter (FIG. 4). The results showed no significant difference between the two groups.

Example 2

2.1 Experimental Procedure

Instead of ZENOAQ's Stem Cell Banker of Example 1, 5% DMSO-containing fetal bovine serum (FBS) (5% DMSO/FBS solution) (DMSO (Sigma), FBS (Gibco)), 10% glycerol-containing fetal bovine serum (FBS) (10% glycerol/FBS solution) (glycerol (Sigma), FBS (Gibco)), or Stem Cell Banker DMSO-free GMP grade (ZENOAQ) was used as the cryoprotectant to freeze and thaw umbilical cord MSCs. The other experimental procedure was performed according to Example 1.

2.2 Results of Experiments

Like in Example 1, the volume of cryoprotective solution remained at the time of cell freezing was much smaller in the pellet method than in the conventional method. In each cryoprotective solution, the cell viability and the cell count after thawing were measured for the conventional method or the pellet method, and no significant differences were observed (FIG. 5).

Example 3

3.1 Experimental Procedure 3.1.1 Conventional Method

Umbilical cord MSCs were frozen and thawed using a FROZEBAG F-050 (NIPRO; volume: 25 ml). Each conical tube containing umbilical cord MSCs (10×10e7 cells) made into single cells by TrypLE™ Select solution was centrifuged at 400 g×5 min. The trypsin solution in the supernatant was removed and then replaced with 20 ml of Stem Cell Banker cryoprotective solution (10% (v/v) DMSO). The entire cell suspension obtained was filled into a FROZE-BAG, placed in a heat insulator Styrofoam box, and subjected to slow freezing overnight at a rate of 0.1 to 1° C./min in a −80° C. freezer. The cells were thawed by warming the bag at 37° C. for several minutes. After the thawing, a syringe was attached to a connector of the bag. The cell suspension was then slowly aspirated from the tube to collect the cells. The cell suspension was transferred to a centrifuge tube, and the cell viability and the cell count were measured with a cell counter. Next, the cell suspension was centrifuged at 400 g×5 min to continue cell culture evaluation. The cryoprotective solution in the supernatant was then removed. After an appropriate amount of each cell culture medium was added, the cells were suspended by pipetting, seeded on a culture dish, and cultured for 3 days. The cells were made into single cells by using TrypLE™ Select solution, and the number of cells was recounted.

3.1.2 Pellet Method

Umbilical cord MSCs were frozen and thawed using a FROZEBAG F-050 (NIPRO; volume: 25 ml). Each conical tube containing umbilical cord MSCs (10×10e7 cells) made into single cells by TrypLE™ Select solution was centrifuged at 400 g×5 min. The trypsin solution in the supernatant was removed and then replaced with 20 ml of Stem Cell Banker cryoprotective solution (10% (v/v) DMSO). The entire cell suspension obtained was filled into a FROZE-BAG, placed in a 4° C. refrigerator for 20 min, and then centrifuged at 400 g×10 min with the bag laterally lying on a multi-well plate rotor TS-41C of TOMY LCX-200 centrifuge. In this way, a cell pellet was formed over a side with a large area of the bag (FIG. 6). Subsequently, the FROZE-BAG was taken out slowly so that the pellet did not float. A syringe was attached to a connector of the bag to remove as much the cryoprotective solution in the supernatant as possible from the tube (about 19 ml in total was removed). The resulting material was placed in a heat insulator Styrofoam box, and subjected to slow freezing overnight at a rate of 0.1 to 1° C./min in a −80° C. freezer. For cell thawing, the bag was subjected to thawing at 37° C. for several minutes. After that, a syringe filled with 20 ml of PBS was set to the tube of the bag. PBS was added to and injected into the bag, and the bag was gently loosened by hand to float the pellet. The cell suspension in the bag was then slowly aspirated, from the tube, with the syringe attached to the connector to collect the cells. The cell suspension was transferred to a centrifuge tube, and the cell viability and the cell count were measured with a cell counter. Next, the cell suspension was centrifuged at 400 g×5 min to continue cell culture evaluation. The PBS in the supernatant was then removed. After an appropriate amount of each cell culture medium was added, the cells were suspended by pipetting, seeded on a culture dish, and cultured for 3 days. The cells were made into single cells by using TrypLE™ Select solution, and the number of cells was recounted.

3.2 Results of Experiments 3.2.1 Volume of Cryoprotective Solution Remained

The volume of cryoprotective solution remained at the time of freezing by the conventional method or the pellet method was calculated from the volume of cryoprotective solution removed from the bag, and plotted in a graph. In the pellet method, the volume remained was reduced to $\frac{1}{20}$ of that in the conventional method (FIG. 7).

3.2.2 Cell Viability and Cell Count

The cell viability and the cell count after thawing by the conventional method or the pellet method were measured, and no significant differences were observed (FIG. 8). The cell count after thawing and the cell count on day 3 of culturing were measured with a cell counter and compared between the conventional method and the pellet method. Then, no significant differences were observed (FIG. 9).

As described above, the pellet method has been demonstrated to have favorable cell cryopreservation efficiency while the volume of cryoprotective solution remained is dramatically decreased. In addition, this method allows cell thawing and syringe filling to be performed in a closed system or in a series of operations, which makes it easy to administer cells to each patient. Further, since the procedure after thawing of cells is only required at a medical site, a cell suspension obtained by this method, for example, can be administered to each patient even in medical facilities without any laboratory.

Hereinabove, the Examples have been described. The Examples are just examples. It should be understood by those skilled in the art that various modifications are allowed and such modified embodiments are within the scope of the invention.

The invention claimed is:

1. A bag containing a composition containing stem cells and a cryoprotectant, wherein the composition forms a cell pellet over a side within the bag.

2. The bag according to claim 1, wherein the cell pellet is formed by centrifuging the bag in a lateral lying position.

3. The bag according to claim 1, wherein the cell pellet is formed so that the cell pellet spreads over the side within the bag.

4. The bag according to claim 1, wherein the composition is a frozen composition.

5. The bag according to claim 1, wherein the composition contains $2.0 \times 10^7$ cells/mL or more cells.

6. The bag according to claim 1, wherein the composition contains 0.5 to 10% (v/v) of the cryoprotectant.

7. The bag according to claim 1, wherein said cell pellet is a cell pellet formed by centrifugation in which centrifugal force is directed toward the side of the bag.

8. The bag according to claim 1, wherein the cell pellet is a cell pellet formed over only one side within the bag.

9. A device comprising a bag according to claim 1 and a syringe, wherein the bag and syringe are integrated.

10. A method of producing a cell suspension for a method of regenerative medicine, comprising the step of adding a solution into the bag according to claim 1 to produce a cell suspension.

11. A cell suspension for a method of regenerative medicine obtained by the production method according to claim 10.

12. A method of regenerative medicine, comprising administering to a subject a cell suspension containing a solution, cells, and a cryoprotectant, wherein the cell suspension is obtained by adding the solution into the bag according to claim 1.

13. The method according to claim 12, comprises the step of adding the solution into the bag, and floating and suspending the cell pellet in the bag by hand unraveling.

14. The method according to claim 12, wherein the solution is saline or buffer solution.

15. A method of producing a stem cell suspension for a method of regenerative medicine, comprising the steps of thawing a frozen composition forming a cell pellet over a side within a bag, wherein the cell pellet contains a frozen cryoprotectant and a frozen single cell population of $2.0 \times 10^7$ cells/ml or more cells to obtain a thawed composition, and adding a solution into the bag containing the thawed composition to produce a stem cell suspension.

16. The method according to claim 15, comprising floating and suspending the thawed composition by hand unraveling.

17. A method of regenerative medicine, comprising administering to a subject a cell suspension containing a solution, cells, and a cryoprotectant, wherein the cell suspension is obtained by the method according to claim 15.

18. The method of regenerative medicine of claim 12, wherein the cryoprotectant content is 0.5% (v/v) or less, and the concentration of cells is $1.0 \times 10^5$ cells/ml or more.

\* \* \* \* \*